(12) United States Patent
Peterson et al.

(10) Patent No.: US 11,871,893 B2
(45) Date of Patent: Jan. 16, 2024

(54) ENDOSCOPIC VISUALIZATION SYSTEM COMPRISING AN ENDOSCOPE, A CABLE AND A MONITOR

(71) Applicant: Conmed Corporation, Utica, NY (US)

(72) Inventors: Eric J. Peterson, Westborough, MA (US); Walter M. DiBacco, Westborough, MA (US)

(73) Assignee: Conmed Corporation, Utica, NY (US)

( * ) Notice: Subject to any disclaimer, the term of this patent is extended or adjusted under 35 U.S.C. 154(b) by 0 days.

(21) Appl. No.: 16/634,371

(22) PCT Filed: Jul. 25, 2018

(86) PCT No.: PCT/US2018/043668
§ 371 (c)(1),
(2) Date: Jan. 27, 2020

(87) PCT Pub. No.: WO2019/023331
PCT Pub. Date: Jan. 31, 2019

(65) Prior Publication Data
US 2021/0093159 A1 Apr. 1, 2021

Related U.S. Application Data

(60) Provisional application No. 62/536,540, filed on Jul. 25, 2017.

(51) Int. Cl.
*A61B 1/04* (2006.01)
*A61B 1/05* (2006.01)
(Continued)

(52) U.S. Cl.
CPC ............ *A61B 1/05* (2013.01); *A61B 1/00006* (2013.01); *A61B 1/00009* (2013.01);
(Continued)

(58) Field of Classification Search
CPC ............ A61B 1/00048; A61B 1/00006; A61B 1/00009; A61B 1/00114; A61B 1/0669;
(Continued)

(56) References Cited

U.S. PATENT DOCUMENTS 7,442,167 B2   10/2008   Dunki-Jacobs et al.
9,526,404 B2   12/2016   Blumenzweig et al.
(Continued)

FOREIGN PATENT DOCUMENTS

CN   102469916 A   5/2012
CN   104545774 A   4/2015
(Continued)

OTHER PUBLICATIONS

JP Office Action, Application No. 2020-503990, dated Mar. 30, 2021, pp. 1-12.
(Continued)

*Primary Examiner* — Howard D Brown, Jr.
(74) *Attorney, Agent, or Firm* — Bond, Schoeneck & King, PLLC; Frederick J. M. Price

(57) ABSTRACT

An endoscopic visualization system (10) includes an endoscopic subsystem (26) comprising an endoscope having an optical channel and an illumination channel, an image sensor operatively coupled to receive light from the optical channel and a solid-state light source operatively coupled to transmit light through the illumination channel; at least one electrical cable extending from the endoscopic subsystem; and a monitor subsystem (12) comprising a frame defining an inner compartment, a display screen and at least one port configured to receive the at least one electrical cable connected to the endoscopic subsystem.

15 Claims, 6 Drawing Sheets

(51) Int. Cl.
*A61B 1/00* (2006.01)
*A61B 1/06* (2006.01)
*H04N 23/74* (2023.01)
*A61B 1/07* (2006.01)
*H04N 23/50* (2023.01)

(52) U.S. Cl.
CPC ...... *A61B 1/00048* (2013.01); *A61B 1/00114* (2013.01); *A61B 1/0655* (2022.02); *A61B 1/0669* (2013.01); *A61B 1/0684* (2013.01); *H04N 23/74* (2023.01); *A61B 1/00108* (2013.01); *A61B 1/042* (2013.01); *A61B 1/07* (2013.01); *H04N 23/555* (2023.01)

(58) Field of Classification Search
CPC ... A61B 1/0684; A61B 1/00108; A61B 1/042; A61B 1/07; A61B 1/05; A61B 1/00045; A61B 1/00124; A61B 1/00172; A61B 1/045; H04N 5/2354; H04N 2005/2255
See application file for complete search history.

(56) References Cited

U.S. PATENT DOCUMENTS

| | | | |
|---|---|---|---|
| 9,531,156 B2 | 12/2016 | Hoffman et al. | |
| 2006/0116553 A1* | 6/2006 | Dunki-Jacobs | A61B 1/07 600/179 |
| 2009/0027492 A1* | 1/2009 | Hibi | A61B 1/00105 348/68 |
| 2010/0228089 A1* | 9/2010 | Hoffman | H01S 5/06808 372/38.07 |
| 2013/0100264 A1* | 4/2013 | Kazakevich | G02B 23/2469 348/68 |
| 2013/0331647 A1* | 12/2013 | Gingras | A61N 5/062 600/109 |
| 2015/0099929 A1* | 4/2015 | Blumenzweig | A61B 1/0669 600/110 |
| 2017/0367569 A1* | 12/2017 | Ohara | A61B 1/0669 |
| 2019/0350438 A1* | 11/2019 | Masuno | G02B 23/24 |
| 2020/0197872 A1* | 6/2020 | Koga | B01D 65/02 |
| 2021/0093159 A1* | 4/2021 | Peterson | A61B 1/0655 |
| 2021/0106211 A1* | 4/2021 | Onobori | A61B 1/0669 |
| 2022/0378284 A1* | 12/2022 | Tabata | A61B 1/0669 |

FOREIGN PATENT DOCUMENTS

| | | |
|---|---|---|
| CN | 105592774 | 5/2016 |
| JP | 1997-292575 A2 | 11/1997 |
| JP | 2005-192739 A2 | 7/2005 |
| JP | 2010012035 | 1/2010 |
| JP | 2012527927 | 11/2012 |
| JP | 2013034546 | 2/2013 |
| JP | 2014033730 | 2/2014 |
| JP | 2016533253 | 10/2016 |
| KR | 10-2006-0122943 | 11/2006 |
| WO | 2017/096316 | 6/2017 |

OTHER PUBLICATIONS

Canada Office Action, Application No. 2070950, pp. 1-4, dated Apr. 12, 2021.
CN Office Action, Application 201880057369.2, dated Dec. 1, 2021, pp. 1-8.
JP Preliminary Rejection, Application No. 10-2022-7002487, dated Mar. 29, 2022, pp. 1-13.
JP Office Action, Application No. 2021-139841, dated Sep. 26, 2022, pp. 1-4.
KR Office Action, App. No. 10-2022-7002487, dated Sep. 20, 2022, pp. 1-4.
CN Office Action, Application No. 201880057369.2, pp. 1-8, dated Jul. 29, 2023.

\* cited by examiner

ENDOSCOPIC VISUALIZATION SYSTEM COMPRISING AN ENDOSCOPE, A CABLE AND A MONITOR

CROSS-REFERENCE TO RELATED APPLICATIONS

The present application claims priority to U.S. Provisional App. No. 62/536,540, filed on Jul. 25, 2017.

BACKGROUND

Endoscopic systems in practice often include at least four separate devices working in concert: a monitor, a light source, a camera control unit and a hand-held portion that may include an image sensor, an endoscope and a camera head. The image sensor may be disposed in the endoscope (typically for chip-on-tip endoscope types) or in the camera head opto-mechanically coupled to the optical type of endoscope. The endoscope typically contains an illumination channel for transmission of the light energy to the surgical sight and an optical channel for forming of the optical image on the image sensor. In use, the distal end of the endoscope is inserted into a patient's bodily cavity. Light enters into the bodily cavity from the light source, via an optical light guide that carries light from the light source to the illumination channel of the endoscope. Light reflects off the body internals and an image is formed on an image sensor disposed in the endoscope or in the camera head. A raw video signal produced by the image sensor is transmitted to the camera control unit via an electrical cable. The camera control unit applies image processing, enhancement and formatting to a standardized video format and transfers the image to the display monitor via the video cable. The surgeon then observes his own actions within the body on the display monitor.

At least three of these devices—the monitor, camera control unit, and light source—are mounted on a stand in the operating room. The hand-held portion is separately attached to the light source and the camera control unit, which itself is connected to the monitor.

As a result, the typical endoscopic system is costly and takes up cart and shelf space in the operating room.

Accordingly, there is a need in the art for an endoscopic system that reduces the cost and the number of required devices to perform surgery.

SUMMARY

This disclosure is generally related to an endoscopic system including an endoscope and a monitor that houses either a camera control unit, a light source driver, or both, thus eliminating one or two of the separate devices typically required to conduct surgery. The resulting integrated endoscopic system reduces complexity, cost, and space.

According to an aspect, an endoscopic visualization system includes an endoscopic subsystem comprising: an endoscope having an optical channel and an illumination channel; an image sensor operatively coupled to receive light from the optical channel; and a solid-state light source operatively coupled to transmit light through the illumination channel; at least one electrical cable extending from the endoscopic subsystem; and a monitor subsystem comprising: a frame defining an inner compartment; a display screen; and at least one port configured to receive the at least one electrical cable connected to the endoscopic subsystem.

In an embodiment, the solid-state light source is powered by a light source driving signal received via the at least one electrical cable.

In an embodiment, the brightness of the solid-state light source is dynamically controlled according to the light source driving signal.

In an embodiment, the endoscopic visualization system further includes light source driver disposed within the inner compartment of the monitor subsystem and configured to generate the light source driving signal.

In an embodiment, the light source driver includes a constant current driver.

In an embodiment, the light source driver includes a buck converter.

In an embodiment, the at least one cable includes a first cable for carrying the driving signal, the first cable being received at a first port of the at least one port, and a second cable, the second cable being received at a second port of the at least one port.

In an embodiment, the second cable is operatively connected to receive from the image sensor an image signal.

In an embodiment, the monitor subsystem further includes a controller disposed within the inner compartment of the monitor subsystem, configured to receive the image signal and to process the image signal.

In an embodiment, the display screen is configured to display an image according to the processed image signal.

According to another aspect, an endoscopic visualization system includes an endoscopic subsystem comprising: an endoscope having an optical channel and an illumination channel; an image sensor operatively coupled to receive light from the optical channel; and a solid-state light source operatively coupled to transmit light through the illumination channel; at least one electrical cable extending from the endoscopic subsystem; and a monitor subsystem comprising: a frame defining an inner compartment; a light source driver disposed within the inner compartment and configured to generate a light source driving signal; a display screen; and at least one port configured to receive the at least one electrical cable connected to the endoscopic subsystem, the at least one port receiving the light source driving signal such that the light source is driving signal is conveyed through the at least one electrical cable to the endoscopic subsystem.

In an embodiment, the light source is powered and its brightness dynamically controlled by the light source driving signal.

In an embodiment, at least one cable comprises a first cable for carrying the driving signal, the first cable being received at a first port of the at least one port, and a second cable, the second cable being received at a second port of the at least one port.

In an embodiment, the second cable is operatively connected to receive from the image sensor an image signal.

In an embodiment, the monitor subsystem further includes a controller disposed within the inner compartment of the monitor subsystem, configured to receive the image signal and to process the image signal.

According to another aspect, an endoscopic visualization system includes: an endoscopic subsystem including an endoscope and being connected to a first end of at least one first cable; a monitor subsystem being connected to a first end of at least one second cable; a terminating adapter being connected to the second end of the at least one first cable and to the second end of the at least one second cable, the terminator being configured to convey a signal between the at least one first cable and the at least one second cable.

In an embodiment, the at least one second cable is dimensioned to permit the terminating adapter to be positioned from remotely from the monitor.

In an embodiment, the terminating adapter is remotely mounted to a structure from the monitor.

In an embodiment, the terminating adapter is mounted to a boom or to cart.

In an embodiment, the terminating adapter is mounted such that the at least one cable descends from above a patient.

In an embodiment, the terminating adapter includes an amplifier to amplify the signal.

In an embodiment, the signal is a light source driving signal originating at a light source driver disposed in a frame of a monitor subsystem wherein the light source driving signal, the light source driving signal, being conveyed from the light source driver to the at least one first cable, powers a solid-state light source operatively connected to the endoscope.

In an embodiment, the signal is an image signal originating at an image sensor operatively connected to the endoscope, the image signal, being conveyed from the light source driver to the at least one second cable, is received at a controller disposed within a frame of a monitor subsystem.

In an embodiment, the at least one first cable comprises a first cable and a second cable, wherein the first cable is connected to the terminating adapter by a first port and the second cable is connected to the adapter by a second port, wherein the at least one second cable comprises a third cable and a fourth cable, wherein the third cable is connected to the terminating adapter by a third port and the fourth cable is connected to the adapter by a fourth port, wherein the terminating adapter is configured to convey the signal between the first cable and the third cable and to convey a second signal between the second cable and the fourth cable.

In an embodiment, the signal is a light source driving signal and the second signal is an image signal.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

FIGURES

In the drawings, like reference characters generally refer to the same parts throughout the different views. Also, the drawings are not necessarily to scale, emphasis instead generally being placed upon illustrating the principles of the invention.

DETAILED DESCRIPTION

Figure 1:
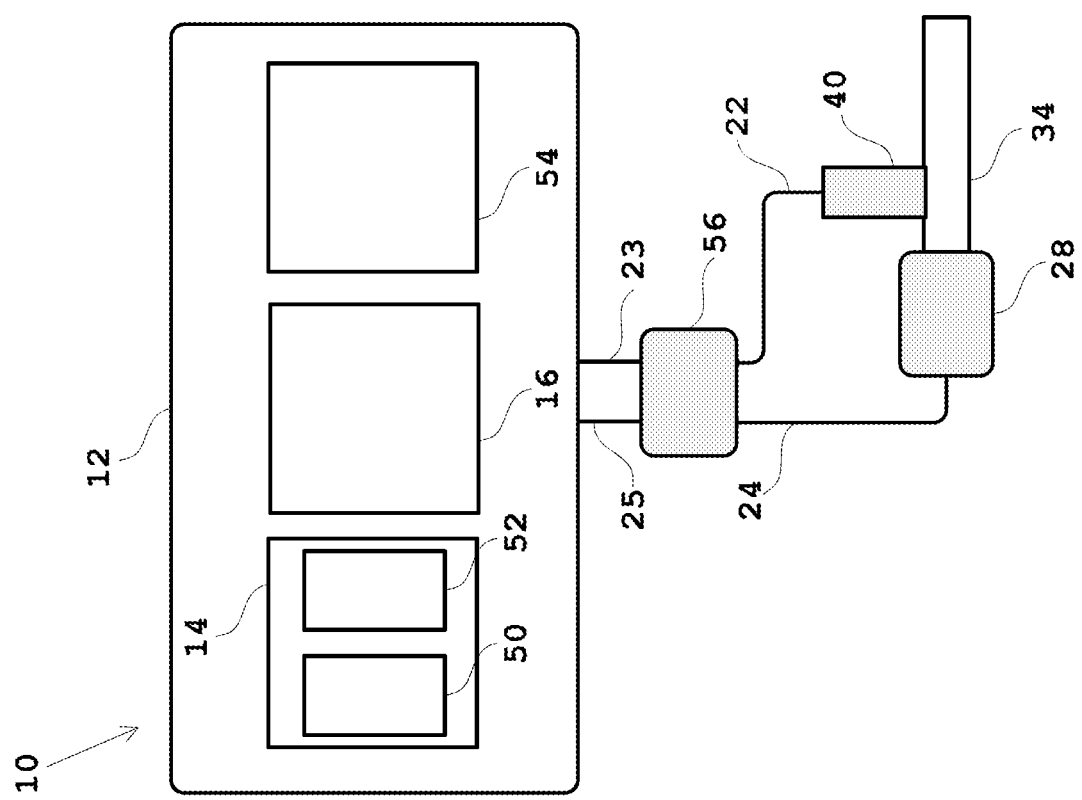
FIG. 1 is a block diagram of an example endoscopic visualization system.

Turning to FIG. 1, there is shown a block diagram of an example endoscopic visualization system 10. That endoscopic visualization system 10, in the example, comprises a monitor subsystem 12 that houses a camera control unit 14, a light source driver 16, and display electronics 54. Monitor subsystem 12 may also include a cable terminator 56, and ports 18, 20 (shown, for example, in FIG. 3) for receiving cables 22, 24 for connection to an endoscopic subsystem 26. Endoscopic subsystem 26 (shown, for example in FIG. 2) includes, in an example, a camera head 28, configured to send and receive signals, via cable 24 and 25, to and from the camera control unit 14, and a light source 40 that is driven by light source driver 16 via a drive signal carried through cable 22 and 23.

Figure 2:
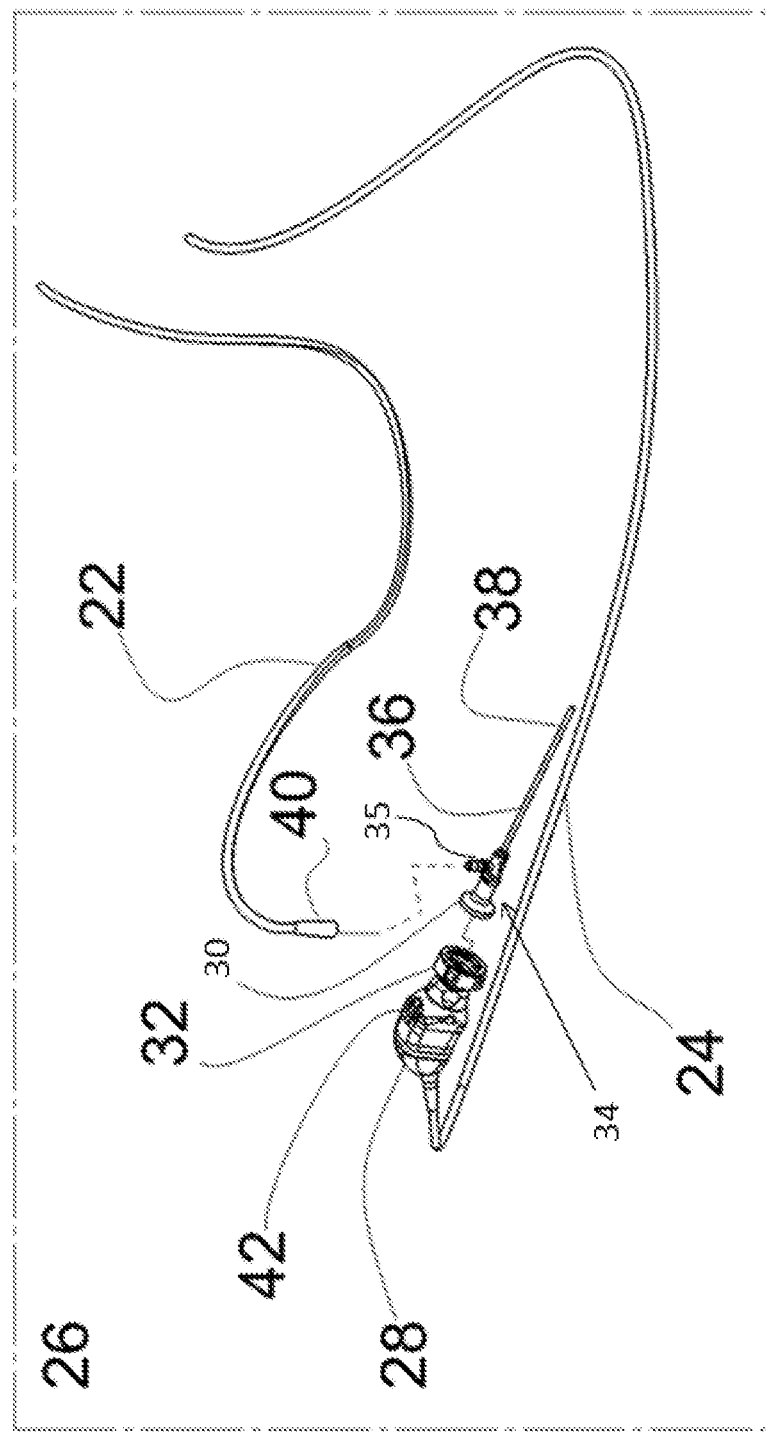
FIG. 2 is a perspective view of an example endoscopic subsystem.

Referring to FIG. 2, endoscopic subsystem 26 includes a camera head 28, an optical coupler 32, and an endoscope 34 with a body 30 a shaft 36 extending from the body 30 terminating in a distal end 38. Shaft 36 may be either rigid or flexible. The shaft 36 may further be sized to be advanced into a patient's bodily cavity, whether naturally existing or surgically created. The endoscope 34 typically defines an illumination channel for transmission of the light energy (e.g., from light source 40) to the surgical sight and an optical channel for forming of the optical image on the image sensor.

As mentioned above, endoscopic subsystem 26 may include a light source 40. Light source 40 is a device that emits light sufficient to the illuminate the bodily cavity into which the endoscope is inserted. In an example, embodiment, the light source 40 is an LED, which offers advantages of size, efficiency, and brightness over other types of light sources; however, in alternate embodiments, the light source 40 may be another kind of solid-state light source, such as a laser diode. In yet another embodiment, the light source 40 may be a light source other than a solid-state light source, such as an incandescent, halogen, etc.

Light source 40 may be operably positioned to transmit light to the distal end 38 of endoscope 34, thus illuminating the bodily cavity during use. For example, light source 40 may be attached along the body 30 or shaft 36—such as at an optical post 35 configured for receiving a light source or optical light guide—and the light emitted by the light source 40 may be collated and redirected down shaft 36 to the distal end 38 by a lens, prism, mirror, or some other reflective or refractive structure. In an alternate embodiment, light source 40 may be incorporated within the body 30 of endoscope 26 and not attached separately. Light source 40 may be otherwise operatively attached or positioned within camera head 28 to direct light to the distal end 38 of endoscope 34.

In an alternate embodiment, instead of being locally connected to or disposed within endoscopic subsystem 26, light source may instead be positioned remotely from endoscopic subsystem 26, either within monitor subsystem 12 (i.e., instead of light source driver 16, monitor subsystem 12 includes the light source 40 itself) or a within a dedicated light source external to monitor subsystem 12. Light source 40, if positioned remotely from endoscopic subsystem 26, may direct light to endoscope through an optical light guide, such as a fiber optic cable, attached to endoscope 34. If light source 40 is a remote dedicated unit, it may be still controlled by monitor subsystem 12 through a control interface. Monitor subsystem 12 may include additional control circuitry for controlling an external light source 40 and may communicate commands, such as dimming level, to the light source 40 via the control interface.

As shown in FIG. 1 and FIG. 2, endoscopic subsystem 26 may further include camera head 28 configured to form an image (when in use, the image will be of a bodily cavity) and optical coupler 32 configured to couple camera head 28 to endoscope 34. Optical coupler 32 may be affixed to camera head 28 or may be removable. The camera head 28 may include an image sensor comprising, for example, a CCD or CMOS chip, configured to receive light and convert it into a camera signal representative of the received light. The camera head may be operatively positioned on or within endoscope 34 to receive light reflected from within the patient's bodily cavity. For example, camera head 28 may be mounted in the body 30 of endoscope 34 or, alternatively, within the shaft 36 or on the distal end 38 of endoscope 34. A reflective or refractive structure, such as a prism, mirror, or lens or may be positioned such that light from within the bodily cavity is incident upon the image sensor of camera head 28. Camera head 28 may be further be mounted with a motor or other actuator to rotate or move within the patient's bodily cavity in order to obtain different views.

Buttons 42 shown in FIG. 2 may be located on top of camera head 28 to control dimming, camera function, fluid removal or other functions of endoscopic visualization system 10.

Figure 3:
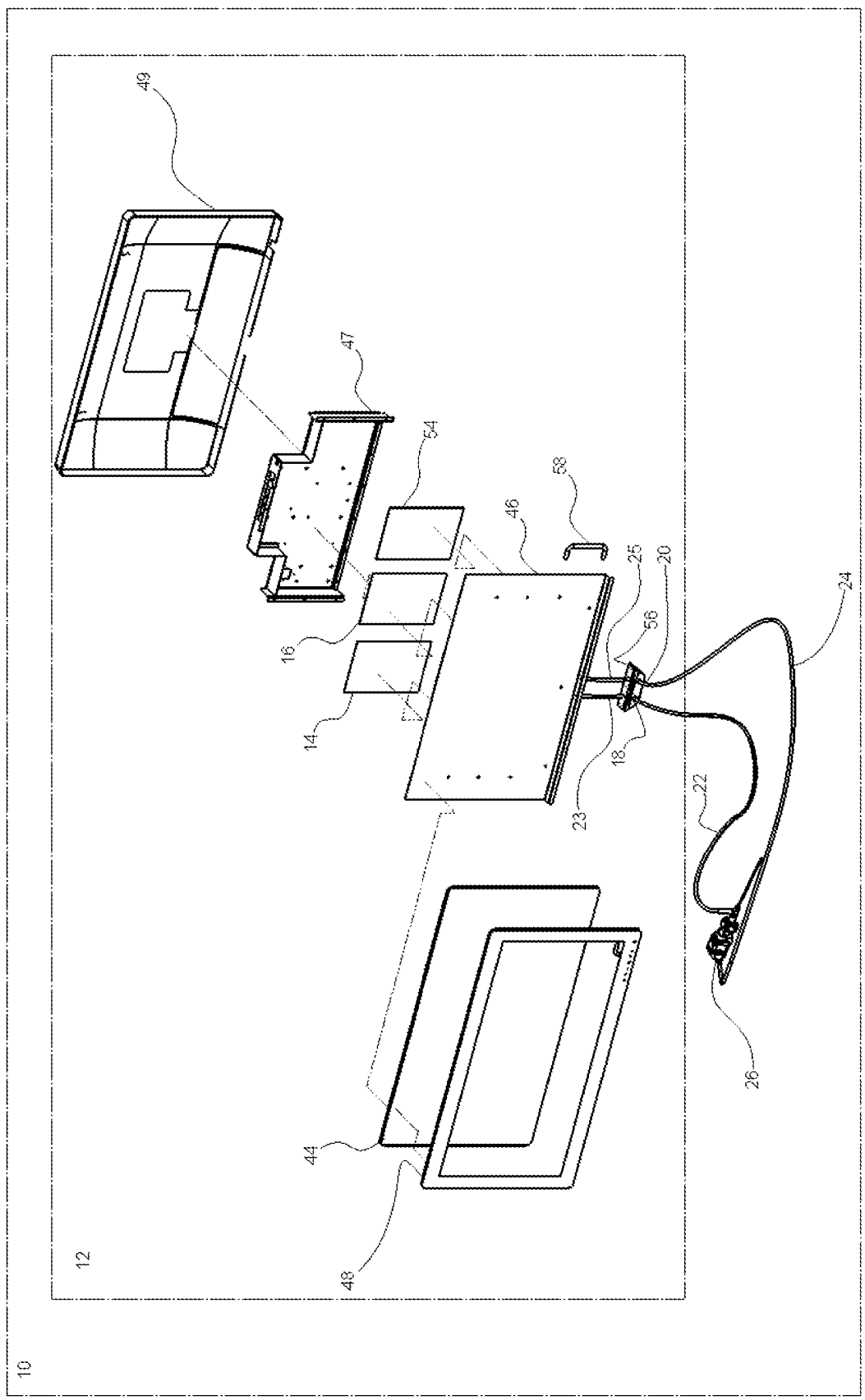
FIG. 3 is an exploded e view of an example endoscopic visualization system.
Figure 4:
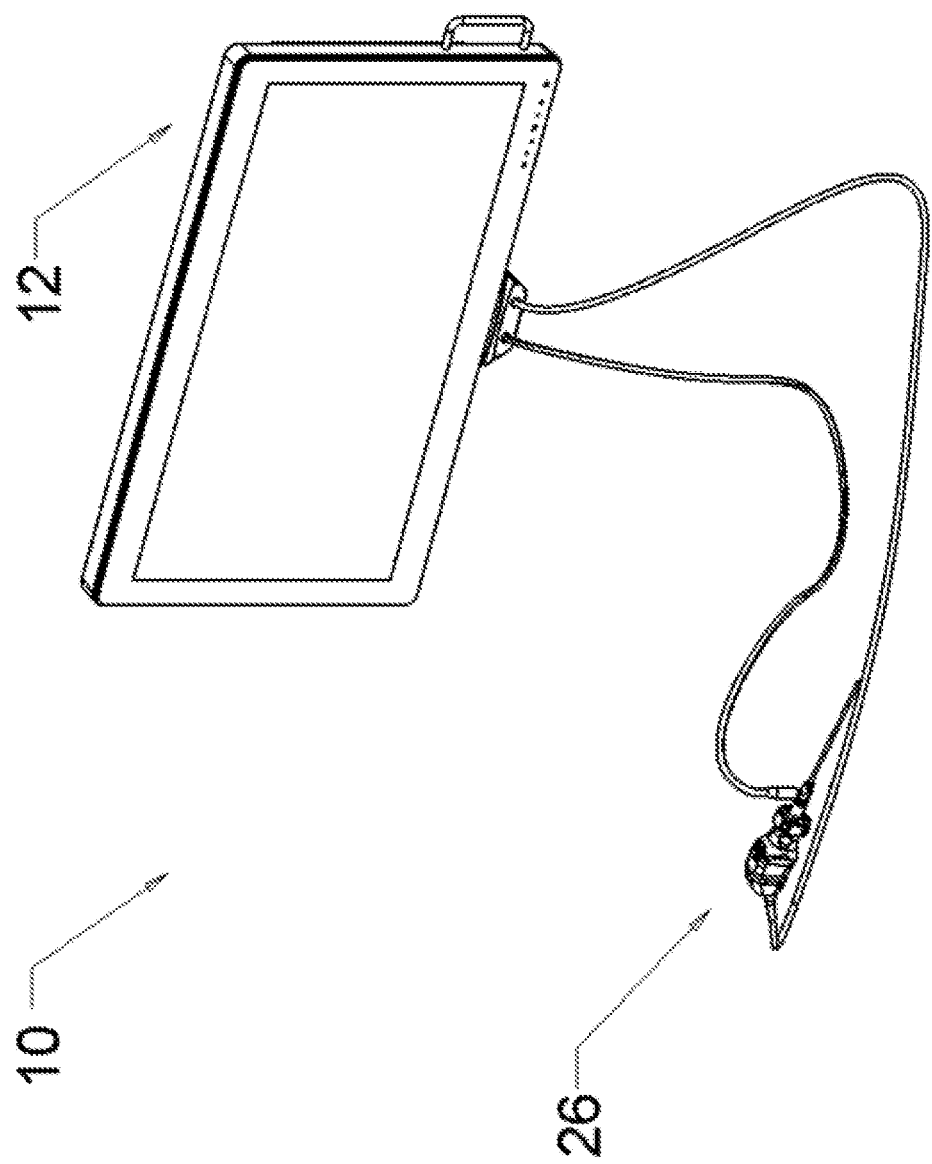
FIG. 4 is a perspective view of an example endoscopic visualization system.

As described above, and referring to FIG. 3 cables 22 and 23 may connect light source 40 to monitor subsystem 12 through port 18. Cables 24 and 25 may connect camera head 28 to monitor subsystem 12 through port 20. Monitor subsystem 12 may include screen 44 and frame 46 and 47 containing a light source driver 16, camera control unit 14, and display electronics 54. More particularly, frame 46 and 47 may define the outer perimeter of monitor subsystem 12 and an inner compartment. For example, frame 46 and 47 together with rear cover 49 typically comprises the back of the monitor and sides that define an outer edge. Monitor subsystem 12 may further include a bezel 48 that holds the screen in place. However, one of ordinary skill will realize that a frame may take a variety of shapes. For example, frame 46 and 47 and rear cover 49 may comprise a curved back that directly meets the bezel 48 at the outer edge, thus eliminating the sides of a more typical rectangular monitor. Similarly, many efforts are in place to minimize the size of the bezel 48, and some embodiments of monitor subsystem 12 may eliminate it entirely. Regardless of these variations, monitor subsystem 12, using, for example, a frame 46 and 47, defines an inner compartment that is either wholly or partially contained within the monitor subsystem 12. As shown in FIG. 3, it is within this inner compartment (which may be comprised of a single compartment or multiple compartments) that light source driver 16, camera control unit 14, and display electronics 54 are housed. (An example of the endoscopic system described in connection with FIGS. 1-3, is further shown in perspective view in FIG. 4.)

Light source driver 16 is a power supply circuit suitable for providing a voltage and current for driving light source 40. In an example embodiment—in which the light source is an LED—the light source driver 16 is an LED driver. For example, the light source driver 16 may be an AC-DC or DC-DC converter. The converter may be switched-mode converter such as a buck converter, a boost converter, a buck-boost converter, or a flyback converter, although other types of power supplies may be used.

In one embodiment, the output of the light source driver 16 may be constant current, rather than pulse-width modulated current. Operating rooms typically have limits on the amount of RF interference that may be generated by the operating equipment. To avoid exceeding these limits, the output from the LED driver should be low frequency with respect to the RF limits of the operating room. A buck converter is one type of power supply outputs a constant current, thus minimizing or eliminating the problematic RF radiation. An LED driver utilizing the buck topology is the TPS92513 1.5-A Buck LED Driver with Integrated Analog Current Adjust available from Texas Instruments. The TPS92513 is merely provided as an example and other LED driving chips may be used.

Light source driver 16 or a supporting circuit within monitor subsystem 12 may identify the performance characteristics of the light source using a local electronic memory system for performance optimization of the light source 40.

Light source 40 may be dimmable through operation of light source driver 16, via, for example, pulse-width modulation or amplitude modulation, the brightness of the LED thus being dynamically controlled. In an alternate embodiment, dimming may occur within the camera head 28 or the cable terminator 56, thus avoiding the need to transmit a pulse-width modulated current or any other signal that may create RF radiation. Dimming may be controlled through buttons 42 located on camera head 28, or, alternatively, through buttons located on monitor subsystem 12 itself or buttons located elsewhere such as on a tablet or remote control device.

Monitor subsystem 12 shown in FIG. 3 may also include camera control unit 14. Camera control unit 14 comprises image processing electronics, which communicate with camera head 28, interpret the camera signal received from camera head, and perform any necessary video processing in order to prepare the camera signal for display on screen 44. Camera control unit 14 may include camera sensor processor 50 and camera system processor 52 as shown in FIG. 1. The camera sensor processor 50 may receive the camera signal from camera head 28 and create, from the camera signal, video data. The video data may be transmitted in any electronic format analog or digital, for example, if digital, any bit depth compressed or uncompressed format. The video data may be received by camera system processor 52, which may apply image enhancement and optimization to display on the surgical image on screen 44. In an example, camera control unit 14 may cooperate with the display electronics 54, additionally disposed in frame 46 and 47, to display the video on the screen 44. Alternatively, camera control unit 14 may be configured to display the video on screen 44 without interfacing with panel electronics 54.

In an alternate embodiment, some of the image processing or all of the image processing performed by camera control unit 14 may be performed in the endoscopic subsystem 26 by either camera head 28 or another image processing unit located within endoscope 34.

Camera head 28 may be operatively connected to camera control unit 14 via cable 24 and 25. Alternately, camera head 28 may transmit signals to camera control unit 14 via a wireless radio interface or optically. For example, the endoscopic subsystem 26 and monitor subsystem 12 may communicate over Bluetooth or Wi-Fi, streaming the camera signal from camera head 28 to monitor subsystem 12. The camera signal and any communications between camera head 28 and camera control unit 14 may be in any data format suitable for such signal or communication.

Endoscopic visualization system 10, monitor subsystem 12, and camera control unit 14 may be controlled through buttons 42 located on camera head 28 or, alternatively, through buttons located on monitor subsystem 12 or elsewhere, such as a tablet or remote control device.

Although cable 22 and cable 24 are shown, it should be understood that cable 22 and cable 24 may be combined into a single cable 24 that carries both the camera signal and the light source driver signal or only one of the signals as the embodiment requires. Further, it should be understood that cable 23 and cable 25 may be combined into a single cable 25 that carries both the camera signal and the light source driver signal or only one of the signals as the embodiment requires. Alternately, cable 23 and cable 25 may extend from monitor subsystem 12 as a single cable and split into cable 24 and 22 that connect to camera head 28 and light source 40, respectively.

As shown in FIG. 3, monitor subsystem 12 may also include a cable terminator 56 including ports 18, 20 for receiving cables 22, 24, respectively. In the embodiment where only a single cable is used—either because both cables 22, 24 have been combined into one, or because camera head communicates with camera control unit wirelessly—only a single port 18 may be used. Terminator 56 may be passive, meaning that it simply passes the signals from camera control unit and/or light source driver 16 to cables 22, 24. Alternately, terminator 56 may be active and include an amplifier for re-driving either the camera signal or driving signal.

In an embodiment, light source driver 16 may be located in terminator 56, or, alternatively, in endoscopic subsystem 26. In these embodiments, a power source must deliver power to terminator 56 or to endoscopic subsystem 26. The power source may, for example, be located within monitor subsystem 12 and may deliver power to terminator 56 or to endoscopic subsystem 26 via cables 22 and 23. The power source may, in alternate embodiments, be a battery or an AC mains source. In yet another embodiment, the power source may be located external to monitor subsystem 12, in, for example, a dedicated power unit, in which case cables 22 and 23 may not extend to monitor subsystem 12, but instead to the dedicated power unit.

Although terminator 56 is shown at bottom of monitor subsystem 12, it should be understood that terminator 56 may be positioned anywhere convenient for surgical settings. For example, terminator 56 may be positioned on top or on the side or back of monitor subsystem 12. In yet another embodiment, monitor may be included on a boom, or other structure, for positioning the terminator 56, for example, above a patient during surgery, such that cables 22, 24 descend from above the user. Further, although both ports 18 and 20 are shown collocated at a single terminator, the ports may be separated to connect to different parts of monitor subsystem 12. For example, one port 18 may be located at a first terminator on one side of monitor subsystem 12, while another port 20 may be located with a second terminator on an opposite side of monitor subsystem 12. Additionally, although ports are shown located within a terminator 56 that extends out from the frame 46 of monitor subsystem 12, in alternate embodiments the ports may be located directly on frame of monitor subsystem 12.

Figure 5:
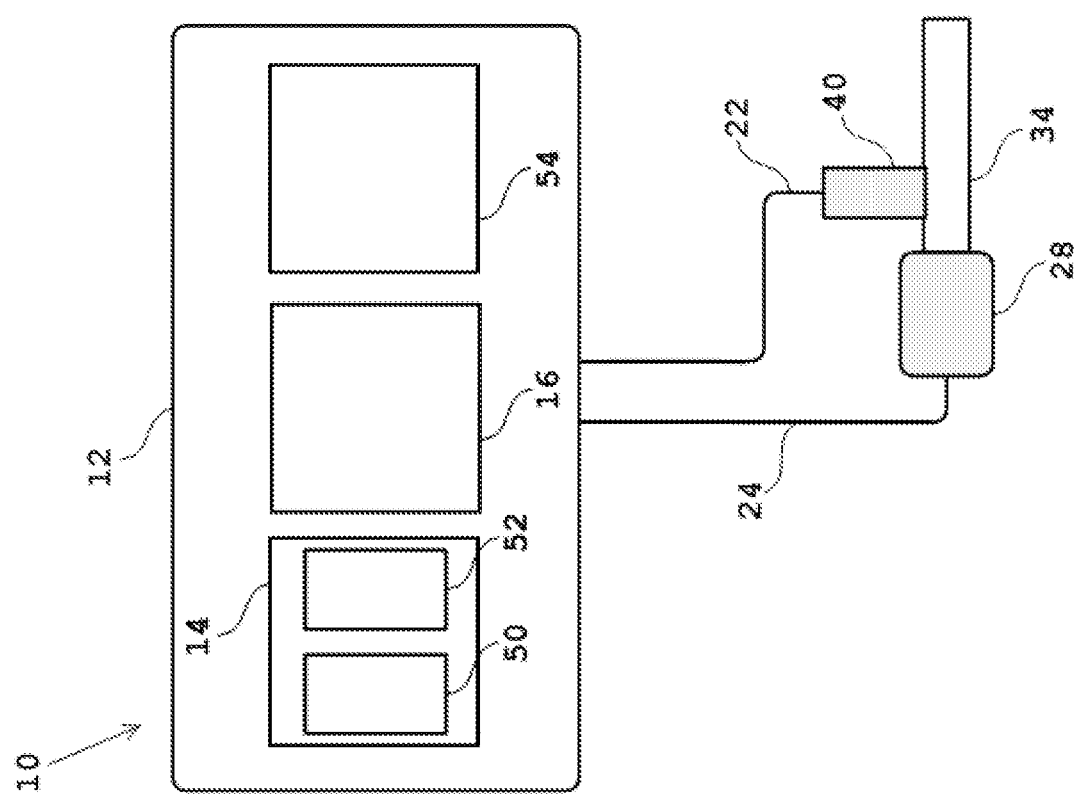
FIG. 5 is a block diagram of an example endoscopic visualization system.
Figure 6:
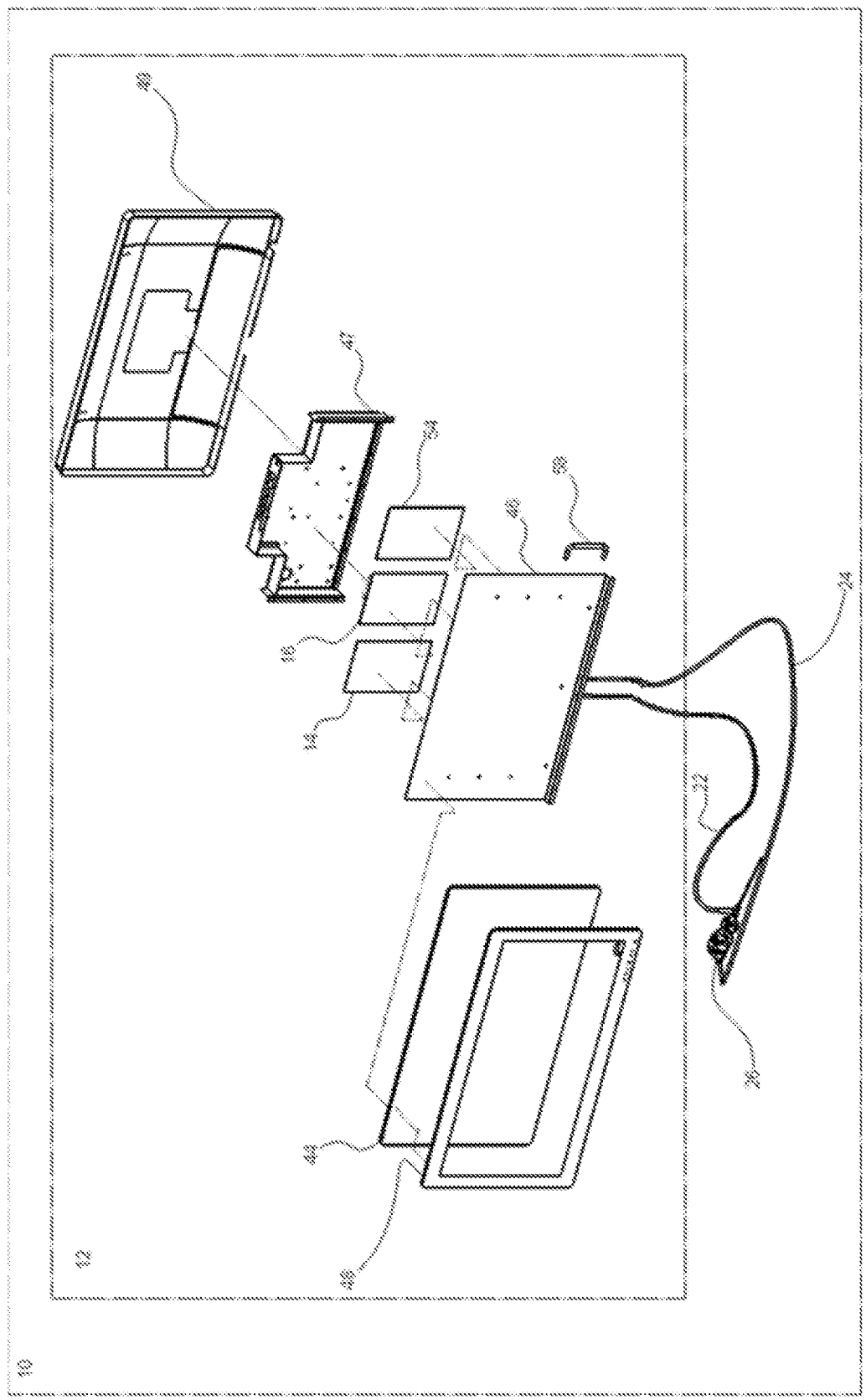
FIG. 6 is an exploded view of an example endoscopic visualization system.

In another embodiment, as shown in FIGS. 5 and 6, the terminator 56 may be omitted completely, and the cables 22 and 24 (or, in another embodiment, single cable 22) may extend directly from monitor subsystem 12 to endoscopic subsystem 26. FIGS. 5 and 6 are otherwise identical to FIGS. 1 and 3, respectively, and so no additional explanation is required.

Monitor subsystem 12 may retransmit the surgical image to additional display monitors using a wired, optical, or wireless transmission method. For example, monitor subsystem 12 may include HDMI ports for receiving an HDMI cable from another display monitor.

Furthermore, monitor subsystem 12 may communicate with other medical equipment via wireless, optical, or wired interfaces to control them or display information as on-screen display. Monitor subsystem 12 may also communicate and be controlled through a mobile device, such as a tablet or a remote control device.

Hand holds 58 may be added to monitor subsystem 12 to aid personnel when inserting or removing cables or repositioning the monitor. In addition, mounting brackets may be added to the monitor subsystem 12 for attaching monitor subsystem 12 to varied surfaces. Mounting brackets may also be added to the monitor subsystem 12 to attach additional equipment to monitor subsystem 12.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. An endoscopic visualization system, comprising:
   an endoscopic subsystem comprising:
      an endoscope body having an optical channel and an illumination channel;
      an image sensor configured to be operatively coupled directly to the endoscope body to receive light from the optical channel; and
      a solid-state light source separate from the endoscope body and the image sensor configured to be operatively coupled directly to an outside portion of the endoscope body to transmit light through the illumination channel and configured to be detachable from the outside portion of the endoscope body;
   at least one electrical cable extending from the endoscopic subsystem; and
   a monitor subsystem comprising:
      a rear cover;
      a frame defining an inner compartment positioned in front of at least a portion of the rear cover, and;
      a display screen positioned in front of at least a portion of the frame; and
      at least one port configured to receive the at least one electrical cable connected to the endoscopic subsystem.

2. The endoscopic visualization system of claim 1, wherein the solid-state light source is powered by a light source driving signal received via the at least one electrical cable.

3. The endoscopic visualization system of claim 2, wherein the brightness of the solid-state light source is dynamically controlled according to the light source driving signal.

4. The endoscopic visualization system of claim 2, further comprising a light source driver disposed within the inner compartment of the monitor subsystem and configured to generate the light source driving signal.

5. The endoscopic visualization system of claim 4, wherein the light source driver comprises a constant current driver.

6. The endoscopic visualization system of claim 5, wherein the light source driver comprises a buck converter.

7. The endoscopic visualization system of claim 4, wherein the at least one cable comprises a first cable for carrying the driving signal, the first cable being received at a first port of the at least one port, and a second cable, the second cable being received at a second port of the at least one port.

8. The endoscopic visualization system of claim 7, wherein the second cable is operatively connected to receive from the image sensor an image signal.

9. The endoscopic visualization system of claim 8, wherein the monitor subsystem further comprises a controller disposed within the inner compartment of the monitor subsystem, configured to receive the image signal and to process the image signal.

10. The endoscopic visualization system of claim 9, wherein the display screen is configured to display an image according to the processed image signal.

11. An endoscopic visualization system, comprising:
an endoscopic subsystem comprising:
an endoscope body having an optical channel and an illumination channel;
an image sensor configured to be operatively coupled directly to the endoscope body to receive light from the optical channel; and
a solid-state light source separate from the endoscope body and the image sensor, configured to be operatively coupled directly to an outside portion of the endoscope body to transmit light through the illumination channel and configured to be detachable from the outside portion of the_endoscope body;
at least one electrical cable extending from the endoscopic subsystem; and
a monitor subsystem comprising:
a rear cover;
a frame defining an inner compartment positioned in front of at least a portion of the rear cover, and;
a light source driver disposed within the inner compartment and configured to generate a light source driving signal;
a display screen positioned in front of at least a portion of the frame; and
at least one port configured to receive the at least one electrical cable connected to the endoscopic subsystem, the at least one port receiving the light source driving signal such that the light source is driving signal is conveyed through the at least one electrical cable to the endoscopic subsystem.

12. The endoscopic subsystem of claim 11, wherein the light source is powered and its brightness dynamically controlled by the light source driving signal.

13. The endoscopic visualization system of claim 11, wherein the at least one cable comprises a first cable for carrying the driving signal, the first cable being received at a first port of the at least one port, and a second cable, the second cable being received at a second port of the at least one port.

14. The endoscopic visualization system of claim 13, wherein the second cable is operatively connected to receive from the image sensor an image signal.

15. The endoscopic visualization system of claim 14, wherein the monitor subsystem further comprises a controller disposed within the inner compartment of the monitor subsystem, configured to receive the image signal and to process the image signal.

\* \* \* \* \*